US00RE39181E

(19) United States
(12) Reissued Patent
François et al.

(10) Patent Number: US RE39,181 E
(45) Date of Reissued Patent: Jul. 11, 2006

(54) AQUEOUS RISPERIDONE FORMULATIONS

(76) Inventors: Marc Karel Jozef François, c/o Janssen Pharmaceutica N.V., Turnhoutseweg 30, Beerse (BE), 2340; Willy Maria Albert Carlo Dries, c/o Janssen Pharmaceutica N.V., Turnhoutseweg 30, Beerse (BE), 2340

(21) Appl. No.: 09/955,274

(22) Filed: Dec. 4, 2001

Related U.S. Patent Documents

Reissue of:
(64) Patent No.: 5,616,587
Issued: Apr. 1, 1997
Appl. No.: 08/429,435
Filed: Apr. 26, 1995

U.S. Applications:
(63) Continuation-in-part of application No. 08/272,462, filed on Jul. 11, 1994, now Pat. No. 5,453,425.

(51) Int. Cl.
*A61K 9/08* (2006.01)

(52) U.S. Cl. ..... 514/258; 514/340
(58) Field of Classification Search ..... 514/258, 514/340
See application file for complete search history.

(56) References Cited

U.S. PATENT DOCUMENTS 5,453,425 A * 9/1995 Francois et al. ..... 514/259.41
6,402,408 B1 * 6/2002 Ferrari ..... 401/64

* cited by examiner

*Primary Examiner*—Thurman K. Page
*Assistant Examiner*—Retford Berko
(74) *Attorney, Agent, or Firm*—Hal B. Woodrow

(57) ABSTRACT

The present invention is concerned with physicochemically stable aqueous solutions of risperidone for oral and parenteral administration; processes for preparing such formulations.

13 Claims, No Drawings

AQUEOUS RISPERIDONE FORMULATIONS

Matter enclosed in heavy brackets [ ] appears in the original patent but forms no part of this reissue specification; matter printed in italics indicates the additions made by reissue.

*This application is a Continuation-In-Part of U.S. application Ser. No. 08/272,462, filed Jul. 11, 1994, now issued as U.S. Pat. No. 5,453,425.*

The present invention is concerned with physicochemically stable aqueous solutions of risperidone for oral and parenteral administration.

EP-0,196,132 (1984) discloses an unbuffered oral solution containing a 1,2-benzisoxazol-3-yl derivative as an antipsychotic ingredient, methylparaben, propylparaben, tartaric acid (ca. 1.37 eq of the active ingredient), sodium saccharin, raspberry and gooseberry essence, the polyhydric alcohols sorbitol and glycerol (1,2,3-propanetriol) and a relatively small amount water (<30% v/v). It further discloses oral drops containing 10 mg/ml of a 1,2-benzisoxazol-3-yl derivative, lactic acid (5.5 eq.), sodium saccharin, cocoa flavour and a very minor amount of water (5% v/v) in polyethylene glycol. Also disclosed is an unbuffered aqueous injectable solution comprising 4 mg/ml of a 1,2-benzisoxazol-3-yl derivative, methylparaben, propylparaben, lactic acid and propylene glycol. The aqueous risperidone formulations of the present invention differ from these prior art formulations in that they are buffered and do not contain sorbitol. Moreover, the present formulations conform more readily to current regulatory requirements.

Regulatory requirements for pharmaceutical preparations over the years have become more stringent. For example, the use of preservatives such as the parabens is nowadays being discouraged. Also stability requirements during storage, when considerable temperature changes may occur which may affect the integrity of the pharmaceutical product, have become more prominent in the regulatory approval phase, imposing new challenges to be faced, and solved, during the development of present day pharmaceutical products. Yet another concern uttered by the authorities relates to the fact that the bioavailability of pharmaceutical products should be predictable and reproducible. For example, this requirement implies that the dissolution behaviour of the product upon oral ingestion, as well as upon injection should be predictable and reproducible.

The present invention relates to the finding that an aqueous buffered solution wherein the benzisoxazole derivative is risperidone has satisfactory oral bioavailability, can be preserved without or with very little preservatives, and can easily be diluted. It relates in particular to the fact that oral solutions were found to have an unsatisfactory physicochemical stability when sorbitol was comprised in the formula. Unexpectedly, sorbitol was found to cause decomposition of risperidone upon storage of the solution at elevated temperatures, i.e. under conditions which imitate those of a long storage time. A similar observation recently made with the polyhydric alcohol maltitol suggests that risperidone may well be incompatible with other polyhydric alcohols. A physico-chemically stable oral risperidone solution was obtained after omitting the sorbitol constituent from the composition. The advantages over the prior art compositions thus are concerned with ease of dilution in other aqueous systems and with improved physicochemical stability.

The present invention concerns an aqueous solution for oral and parenteral administration comprising water, risperidone or a pharmaceutically acceptable acid addition salt thereof, characterized in that said solution comprises a buffer to maintain the pH in the range of 2 to 6 and is essentially free of sorbitol.

The subject compositions are characterized by their improved physicochemical stability when compared to the art compositions. The term "physicochemically stable" as herein defined refers to a solution wherein, after storage for a period up to 4 weeks at a temperature of 80° C. or below, the residual amount of risperidone is 80% or more of the initial risperidone concentration. Several compositions of the subject invention are characterized by an unchanged concentration of risperidone under even more stringent conditions, in particular an extended storage time at an elevated temperature.

Hereinafter, the amounts of each of the ingredients in the compositions are expressed as percentages by weight based on the total volume of the formulation (w/v), or as volume or weight per ml of final solution. Ratios are intended to define weight-by-weight ratios.

Risperidone is genetic to 3-[2-[4-(6-fluoro-1,2-benzisoxazol-3-yl)-1-piperidinyl]ethy1]-6,7,8,9-tetrahydro-2-methyl-4H-pyrido[1,2-a]pyrimidin-4-one. The preparation and pharmacological activity thereof are described in EP-0,196, 132. The term risperidone as used herein comprises the free base form and the pharmaceutically acceptable acid addition salts thereof. The solubility of risperidone is increased upon the formation of such salt forms, which can be obtained by reaction of the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which risperidone as well as the salts thereof, are able to form. Such solvates are for example hydrates, alcoholates and the like.

The solutions according to the present invention have a pH from 2 to 6, preferably from 3 to 5. Oral solutions most preferably have a pH value from 3 to 4, parenteral solutions from 5 to 6. The pH of the compositions is maintained by a buffer system. Buffer systems comprise mixtures of appropriate amounts of an acid such as phosphoric, succinic, tartaric, lactic, or citric acid, and a base, in particular sodium hydroxide or disodium hydrogen phosphate. Ideally, the buffer has sufficient capacity to remain in the intended pH range upon dilution with a neutral, a slightly acidic or a slightly basic beverage.

The desired pH range is most advantageously obtained using a tartaric acid/sodium hydroxide buffer, particularly in view of the fact that risperidone tartrate is the salt form that presently would appear to have the best solubility in aqueous media, in particular upon dilution. Thus, the solubility of risperidone tartrate is about 80 mg/ml, or about 4 times that of risperidone hydrochloride (19.6 mg/ml) at room temperature.

The amount (w/v) of risperidone in the present compositions ranges from 0.01% to 1%, preferably from 0.02% to 0.5%, most preferably from 0.05% to 0.25%, and in particular is 0.1% (1 mg/ml) in the oral solutions and about 0.2% (2 mg/ml) in the parenteral solutions.

In order to prevent the growth of micro-organisms such as bacteria, yeasts and fungi in the oral compositions which are likely to be used repeatedly, a preservative agent may be added. Suitable preservatives should be physicochemically stable and effective in the pH range mentioned above. They comprise benzoic acid, sorbic acid, methylparaben, propylparaben, imidazolidinyl urea (=Germall 115®) and diazolidinyl urea (=Germall II®), phenoxetol, benzyl alcohol, quaternary compounds, e.g. benzylalkonium chloride, and the like. Some preservatives, such as benzoic acid, sorbic acid, Germall 115®, Germall II® and benzyl alcohol, have the advantage that they yield clear, transparent solutions which do not show any clouding upon storage. The concentration of the preservatives may range from 0.05% to 1%, particularly from 0.1% to 0.5%, and most particularly is about 0.2%. The most preferred preservative is benzoic acid used at about 2 mg/ml.

Parenteral solutions do not require the presence of any preservatives. The parenteral solution is sterilized following art-known procedures, e.g. it can be filtered aseptically through a stainless-steel filter holder equipped with a 0.2 μm polyvinylidene difluoride filter into a suitable sterile glass flask, filled into ampoules (e.g. 2 ml), and then sterilized by autoclaving during 30 minutes at 121° C.($^{F}$10,121≧15 min).

The oral compositions optionally may include additional ingredients known in the art of formulation such as sweetening agents, flavouring substances, solubility enhancers, viscosity regulating agents and the like ingredients. For example, the aqueous solubility of the active ingredient may be enhanced by the addition to the solution of a pharmaceutically acceptable co-solvent, a cyclodextrin or a derivative thereof.

The bitter taste of risperidone and the buffer, and the unpleasant taste associated with the pH of some formulas optionally may be masked by one or more intense sweetening agents such as saccharin, sodium or potassium or calcium saccharin, acesulfame potassium or sodium cyclamate. The concentration of the sweetening agent may range from 0.04% to 0.15% and in particular is about 0.1%. Given the incompatability of risperidone with sorbitol, it is believed that the solution should not comprise polyhydric alcohols such as mannitol, fructose, sucrose, maltose and the like sweetening agents. The palatability of the subject solutions optionally may be optimized further by the addition of one or more flavouring substances. Suitable flavouring substances are fruit flavours such as cherry, raspberry, black currant or strawberry flavour, or stronger flavours, such as Caramel Chocolate flavour, Mint Cool flavour, Fantasy flavour and the like. Combinations of flavours are advantageously used. A combination of two cherry flavours was found to yield very good taste masking results in the present compositions. The total concentration of the flavouring substances may range from 0.01% to 0.5%, preferably from 0.03% to 0.2% and most preferably from 0.05% to 0.1%.

The buffered solutions according to the present invention are well suited to dilution with water and beverages or drinking liquids such as coffee, tea, soft drinks and the like. In general this increases the palatability of the oral solution and, hence, patient compliance to the medication.

A particular oral composition according to the present invention comprises (a) 0.02% to 0.5% risperidone;

(b) 0.1% to 0.5% preservatives;

(c) a suitable amount of buffer to adjust the pH in the range from 2 to 6; and (d) water.

The most preferred oral composition according to the present invention contains (a) 0.1% (1 mg/ml) risperidone;

(b) 0.2% (2 mg/ml) benzoic acid;

(c) 0.75% (7.5 mg/ml) tartaric acid and sufficient sodium hydroxide 1 N to adjust the pH in the range from 2 to 6 (approx. 1 mg/ml); and (d) water q.s. ad 100% (1 ml).

Parenteral compositions according to the present invention preferably comprise one or more isotonizing agents, in particular sodium chloride, in amount sufficient to render the final solution isotonic with the body fluid of the subject to be treated. The most preferred parenteral composition according to the present invention contains (a) 0.2% (2 mg/ml) risperidone;

(b) 0.5% (5 mg/ml) sodium chloride;

(c) 0.75% (7.5 mg/ml) tartaric acid and sufficient sodium hydroxide 1 N to adjust the pH in the range from 2 to 6 (approx. 3.5 mg/ml); and (d) water q.s. ad 100% (1 ml).

In a further aspect, the present invention relates to a process of preparing solutions of risperidone as described hereinabove, characterized by dissolving the active ingredient risperidone, either the preservative or the isotonizing agent, and the acid and base components of the buffer in water.

In particular, the process comprises the following steps: (a) adding the acid component of the buffer and the active ingredient risperidone to an amount of water which is preferably above room temperature (b) stirring the mixture until complete dissolution and cooling the solution to room temperature, (c) adjusting the pH with the base component of the buffer and (d) further diluting the solution with water to the required end-volume. In the preparation of oral solutions, step (a) may be preceded by the steps of dissolving the preservative in an amount of heated water and (b) diluting the solution with about an equal amount of water. Optionally, one or more sweetening agents and flavouring substances may be added during any of the process steps. In the preparation of parenteral solutions, step (d) may be preceded immediately by the step of rendering the solution isotonic by the addition of an appropriate amount of an isotonizing agent, and followed by autoclaving.

The following examples are intended to illustrate the scope of the present invention in all its aspects but not to limit it thereto.

EXAMPLE 1

F1: oral solution (pH = 3 ± 1)

| Ingredient | Quantity, mg/ml oral solution |
|---|---|
| risperidone | 2 |
| tartaric acid | 7.5 |
| benzoic acid | 2 |
| Cherry flavour 1 | 0.25 |
| Cherry flavour 2 | 0.5 |
| sodium saccarin | 1 |
| sodium hydroxide | ca. 1 (q.s. ad pH 3 ± 1) |
| purified water | q.s. ad 1 ml |

(1) 2 mg benzoic acid was dissolved in 0.5 ml water upon stirring at 80°–90° C. 0.4 ml water was added to the solution and 7.5 mg tartaric acid and 2 mg risperidone were dissolved in the resulting mixture upon stirring.

(2) 1 mg sodium saccharin was dissolved in 0.05 ml water upon stirring.

(3) fractions (1) and (2) were mixed upon stirring and the solution was cooled to room temperature.

(4) 0.25 mg Cherry flavour 1 and 0.5 mg Cherry flavour 2 were added to fraction (3) upon stirring.

(5) 1 mg sodium hydroxide was added to fraction (4) to adjust the pH to about 3.

(6) fraction (5) was further diluted with water to 1 mL.

In a similar way there were prepared:

| Ingredient | Quantity, mg/ml oral solution |
|---|---|
| F2: oral solution (pH = 4 ± 1) | |
| risperidone | 0.5 |
| tartaric acid | 7.5 |
| benzoic acid | 2 |
| Cherry flavour 1 | 0.25 |
| Cherry flavour 2 | 0.5 |
| sodium saccarin | 1 |
| sodium hydroxide | q.s. ad pH = 4 ± 1 |
| purified water | q.s. ad 1 ml |
| F3: oral solution (pH = 3) | |
| risperidone | 0.5 |
| tartaric acid | 7.5 |
| sodium chloride | 5 |
| sodium saccharin | 1 |
| sodium hydroxide | q.s. ad pH = 3 |
| purified water | q.s. ad 1 ml |
| F4: oral solution (pH = 5) | |
| risperidone | 0.5 |
| tartaric acid | 7.5 |
| sodium chloride | 5 |
| sodium saccharin | 1 |
| sodium hydroxide | q.s. ad pH = 5 |
| purified water | q.s. ad 1 ml |
| F5: oral solution (pH = 3) | |
| risperidone | 1 |
| tartaric acid | 7.5 |
| benzoic acid | 2 |
| sodium hydroxide | ca. 1 (q.s. ad pH = 3) |
| purified water | q.s. ad 1 ml |
| F6 parenteral solution (pH = 5) | |
| risperidone | 2 |
| tartaric acid | 7.5 |
| sodium chloride | 5 |
| sodium hydroxide | ca. 3.75 (q.s. ad pH = 5) |
| purified water | q.s. ad 1 ml |

EXAMPLE 2

The tables hereinbelow summarize the risperidone concentrations measured after a particular storage time of the composition at a particular temperature, expressed as the percentage of the initial risperidone concentration.

| | | F1 | F2 |
|---|---|---|---|
| 4° C. | 12 months | 98.2 | |
| 25° C. | 1 month | 100.4 | 101.1 |
| | 3 months | 102.1 | 99.1 |
| | 6 months | 100.9 | |
| | 9 months | 99.5 | |
| | 12 months | 98.7 | |

-continued

| | | F1 | F2 |
|---|---|---|---|
| 30° C. | 3 months | 102.1 | 98.8 |
| | 6 months | 100.3 | |
| | 12 months | 98.9 | |
| 40° C. | 1 month | 102.1 | 101.1 |
| | 3 months | 100.9 | 99.4 |
| | 6 months | 100.5 | |
| | 12 months | 98.3 | |
| 60° C. | 1 month | 100.1 | 100.3 |

EXAMPLE 3

TABLE 2

| | | F3 | F4 |
|---|---|---|---|
| 80° C. | 5 days | 97.9 | 99.0 |
| | 17 days | 96.7 | 96.6 |
| | 4 weeks | 86.2 | 87.6 |

The data in the tables indicate that compositions F1–F4 satisfy the criteria as set forth hereinbefore to qualify as a "physiochemically stable" composition.

We claim:

1. An aqueous solution suitable for oral and parenteral administration comprising water, risperidone or a pharmaceutically acceptable acid addition salt thereof, characterized in that said solution comprises a buffer to maintain the pH in the range of 2 to 6 and is essentially free of sorbitol.

2. A solution according to claim 1 wherein said pH range is obtained with a tartaric acid/sodium hydroxide buffer.

3. A solution according to claim 1 wherein the amount of risperidone ranges from 0.01% to 1% by weight based on the total volume of the solution.

4. A solution according to claim 1 having a pH ranging from 3 to 4 which is suitable for oral administration.

5. A solution according to claim 4 further comprising benzoic acid as a preservative.

6. A solution according to claim 5 containing (a) 1 mg/ml risperidone;

(b) 2 mg/ml benzoic acid;

(c) 7.5 mg/ml tartaric acid and sufficient sodium hydroxide to adjust the pH in the range from 3 to 4; and (d) water q.s. ad 1 ml.

7. A solution according to claim 6 further comprising one or more members selected from the group consisting of sweetening agents and flavouring substances.

8. A solution according to claim 1 having a pH ranging from 5 to 6 which is suitable for parenteral administration.

9. A solution according to claim 4 further comprising sodium chloride as an isotonizing agent.

10. A solution according to claim 9 containing (a) 1 mg/ml risperidone;

(b) 5 mg/ml sodium chloride;

(c) 7.5 mg/ml tartaric acid and sufficient sodium hydroxide to adjust the pH in the range from 5 to 6; and (d) water q.s. ad 1 ml.

11. A process of preparing a solution according to claim 1 comprising the steps of (a) adding the acid component of the buffer and the active ingredient risperidone to an amount of water, (b) stirring the mixture until complete dissolution and cooling the solution to room temperature, (c) adjusting the pH with the base component of the buffer, and (d) further diluting the solution with water to the required end-volume.

12. A process according to claim 11 for preparing an oral solution as defined in claim 5 wherein step (a) is preceded by the steps of:

(a) dissolving the preservative in an amount of heated water, and (b) diluting the solution with about an equal amount of water.

13. A process according to claim 11 for preparing an parenteral solution as defined in claim 9 wherein step (d) is preceded immediately by the step of rendering the solution about isotonic by the addition of an appropriate amount of isotonizing agent, and is followed by autoclaving.

* * * * *